United States Patent [19]
Allan et al.

[11] Patent Number: 5,788,689
[45] Date of Patent: Aug. 4, 1998

[54] PROSTHETIC HEART VALVE ROTATOR TOOL

[75] Inventors: Bob Allan, Maple Grove; Kimberly A. Anderson, Eagan; William R. Holmberg, St. Paul; Kurt D. Krueger, Stacy; Michael J. Girard, Lino Lakes; Thomas G. Schoon, Cedar; Gary G. Rushmeyer, Marine on St. Croix, all of Minn.

[73] Assignee: St. Jude Medical, Inc., St. Paul, Minn.

[21] Appl. No.: 594,972

[22] Filed: Jan. 31, 1996

[51] Int. Cl.⁶ .......................... A61B 17/00; A61F 2/24
[52] U.S. Cl. ........................................... 606/1; 623/2
[58] Field of Search ............................ 606/1, 99; 623/2; 81/57.26–57.31

[56] References Cited

U.S. PATENT DOCUMENTS

| | | |
|---|---|---|
| Re. 30,507 | 2/1981 | Kastner . |
| 3,587,115 | 6/1971 | Shiley . |
| 3,628,535 | 12/1971 | Ostrowsky et al. . |
| 3,763,548 | 10/1973 | Anderson . |
| 3,800,403 | 4/1974 | Anderson et al. . |
| 3,839,741 | 10/1974 | Haller . |
| 3,959,827 | 6/1976 | Kaster . |
| 3,997,923 | 12/1976 | Possis . |
| 4,078,268 | 3/1978 | Possis . |
| 4,197,593 | 4/1980 | Kaster et al. . |
| 4,276,658 | 7/1981 | Hanson et al. . |
| 4,362,072 | 12/1982 | Tillman . |
| 4,453,434 | 6/1984 | Lissy . |
| 4,455,896 | 6/1984 | Holmes . |
| 4,510,825 | 4/1985 | Neron et al. . |
| 4,535,483 | 8/1985 | Klawitter et al. ........................ 623/2 |
| 4,599,081 | 7/1986 | Cohen ........................................ 623/2 |
| 4,602,911 | 7/1986 | Ahmadi et al. ........................... 623/2 |
| 4,655,462 | 4/1987 | Balsells . |
| 4,680,031 | 7/1987 | Alonso ..................................... 623/2 |
| 4,683,883 | 8/1987 | Martin . |
| 4,705,516 | 11/1987 | Barone et al. ............................ 623/2 |
| 4,790,843 | 12/1988 | Carpentier et al. ...................... 623/2 |
| 4,813,308 | 3/1989 | Petrus . |
| 4,826,144 | 5/1989 | Balsells . |
| 4,863,460 | 9/1989 | Magladry ................................. 623/2 |
| 4,892,017 | 1/1990 | Kennedy et al. . |
| 4,907,476 | 3/1990 | Singleton . |
| 4,915,366 | 4/1990 | Balsells . |
| 4,970,918 | 11/1990 | Brewer et al. . |
| 4,982,727 | 1/1991 | Sato . |
| 5,035,709 | 7/1991 | Wieting et al. .......................... 623/2 |
| 5,058,463 | 10/1991 | Wannop . |
| 5,071,431 | 12/1991 | Sauter et al. ............................. 623/2 |
| 5,104,406 | 4/1992 | Curcio et al. ............................ 623/2 |
| 5,178,633 | 1/1993 | Peters ....................................... 623/2 |
| 5,197,980 | 3/1993 | Gorshkov et al. ....................... 623/2 |
| 5,201,255 | 4/1993 | Gegg . |
| 5,354,330 | 10/1994 | Hanson et al. ........................... 623/2 |
| 5,403,305 | 4/1995 | Sauter et al. ............................. 606/1 |
| 5,480,425 | 1/1996 | Ogilive ..................................... 623/2 |
| 5,582,607 | 12/1996 | Lackman .................................. 606/1 |

*Primary Examiner*—Glenn K. Dawson
*Attorney, Agent, or Firm*—Westman, Champlin & Kelly, P.A.

[57] ABSTRACT

A prosthetic heart valve rotator tool operates in the small chest cavity available to the surgeon, having parts that can be easily assembled and disassembled, allowing it to be cleaned and sterilized for repeated use.

12 Claims, 11 Drawing Sheets

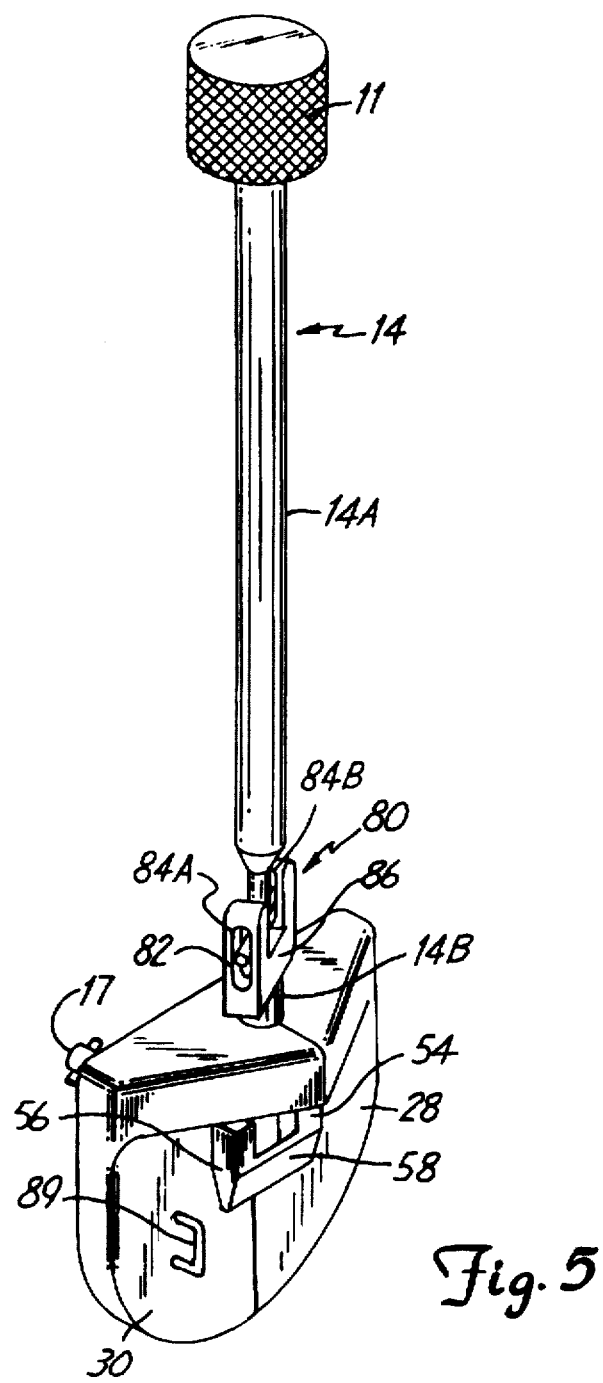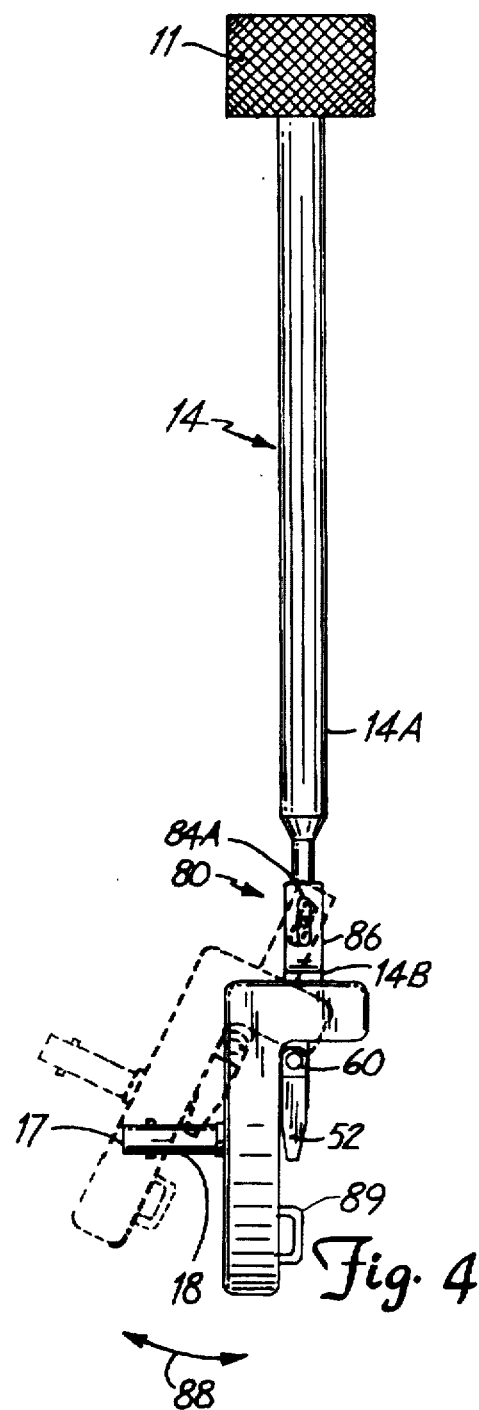

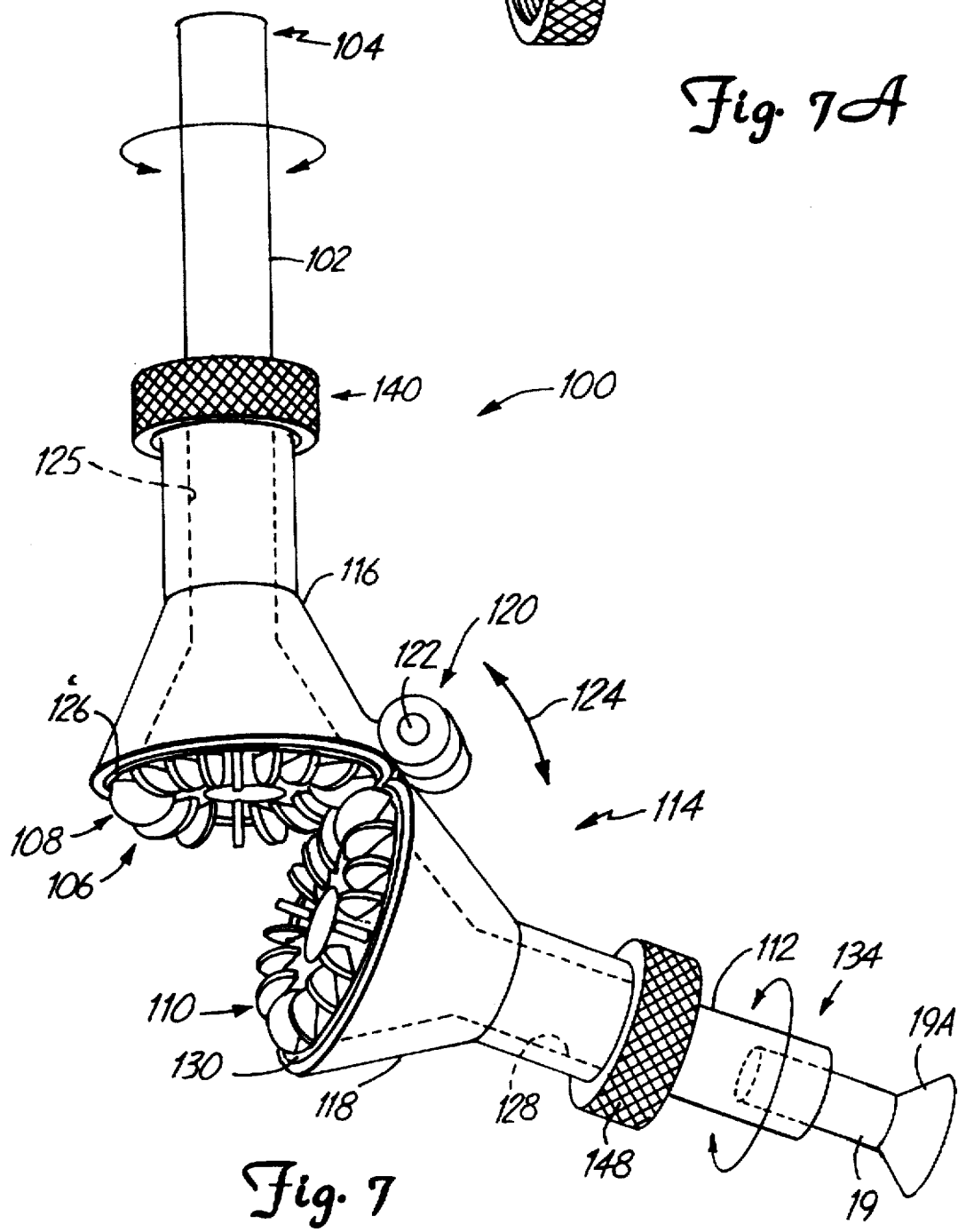

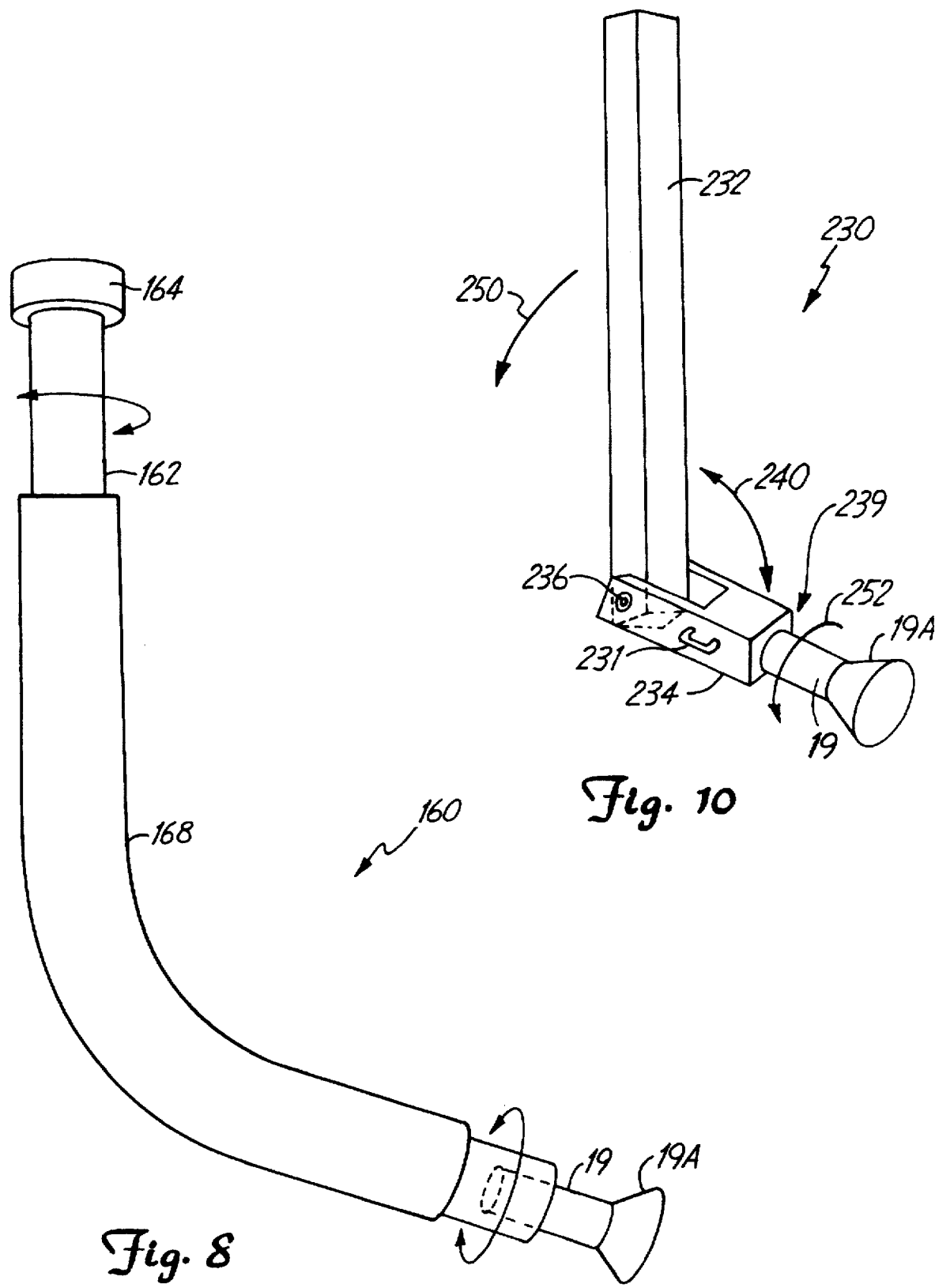

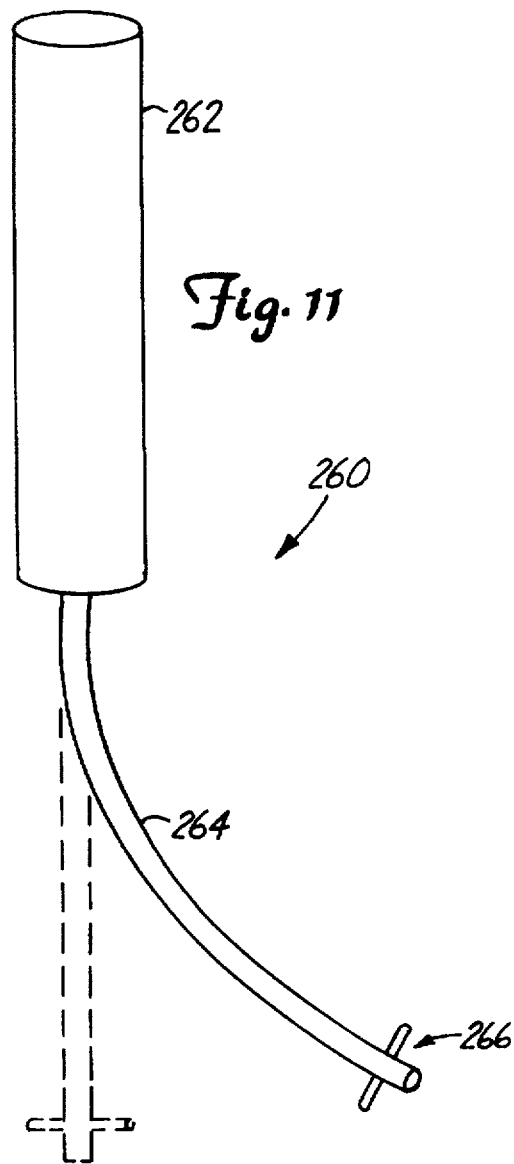
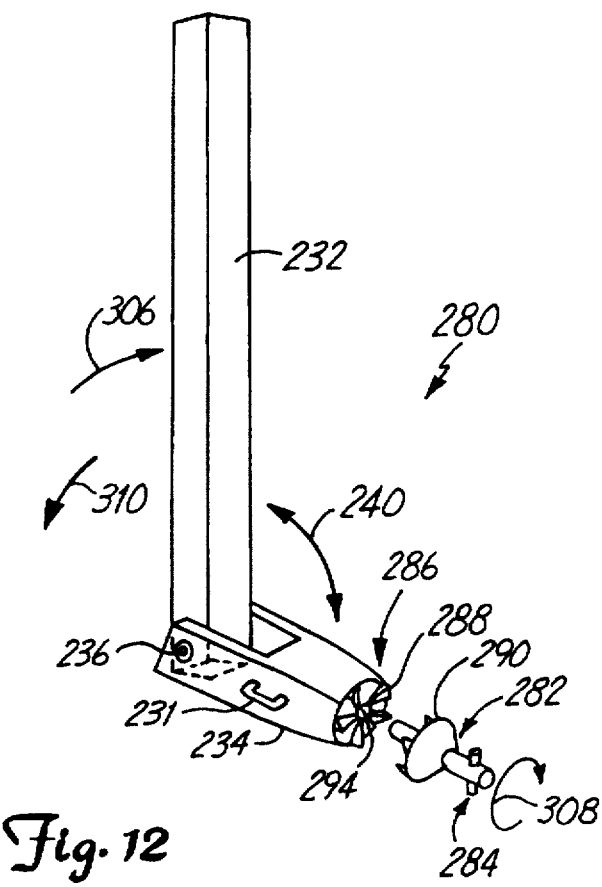

PROSTHETIC HEART VALVE ROTATOR TOOL

FIELD OF THE INVENTION

The present invention relates to surgical instruments. More particularly, the present invention relates to a prosthetic heart valve rotator tool to orient a prosthetic heart valve into a preferred position during surgery.

BACKGROUND OF THE INVENTION

An implantable prosthetic heart valve is used as a replacement for an excised native heart valve of a patient. A typical prosthetic heart valve includes an annular valve orifice or body to provide a passageway for blood. At least one, and usually two, leaflets are mounted to an inner surface of the annular valve body and open or close with the flow of blood through the passageway.

A suture ring or sewing cuff is used to attach the heart valve to the patient's heart tissue. The sewing cuff is secured about the heart valve body in a circumferential groove and generally includes a biocompatible fabric that allows a needle and suture to pass through. The sewing cuff is placed proximate the tissue annulus at the site of the excised native heart valve. Sutures are passed through the tissue annulus and the sewing cuff and tied snugly, thereby securing the valve to the heart.

Prosthetic heart valves are implanted wholly or partially within the tissue annulus of the excised native valve. In some circumstances, a surgeon will need to rotate the prosthetic heart valve so that the leaflets open and close properly. This is done as the sewing cuff is sutured to the heart tissue, or if the sewing cuff is rotatable relative to the valve, this can be done after the sewing cuff is secured to the heart tissue. Pending U.S. patent application 08/327,164, filed Oct. 21, 1994, entitled "ROTATABLE CUFF ASSEMBLY FOR A HEART VALVE PROSTHESIS" and incorporated herein by reference, discloses a sewing cuff assembly having a resiliently deformed spring disposed along an annular seat of the valve body. The spring exerts a controlled force on the valve body, which results in a rotation-resisting torque when an outside force is applied to the valve. The rotation-resisting torque is sufficient to resist rotation during normal operation of the valve after implantation but low enough to permit the surgeon to rotate the valve during implantation.

However, in some instances, rotation of the prosthetic heart valve may be encumbered by lack of available space in which the surgeon has to work, especially in the case of small patients, for example, children. The lack of space is particularly prevalent when a prosthetic heart valve will be sutured in place of a native mitral valve.

FIG. 16 is a schematic diagram generally illustrating the difficulties involved with orienting a prosthetic mitral valve 1 during surgery. In FIG. 16, a patient's open chest is represented by plane ABCD. The patient is lying on an operating table represented by plane EFQR. A surgeon faces the patient and is generally parallel to plane ADFE. Although the chest is open, the surgeon only has access to the prosthetic mitral valve 1 (generally lying in a plane KLMN) through a small access aperture 2 bounded by line segments ADOP. The access aperture 2 opens to a small cavity proximate a plane GHIJ, which represents access to the patient's atrium 3. In FIG. 16, line segment ER extends perpendicular through the patient's sternum, while planes ADFE and BCQR represent the patient's right and left lung, respectively. To successfully rotate the prosthetic mitral valve 1, the surgeon must break the plane GHIJ and engage the prosthetic mitral valve 1 at plane KLMN through the atrium 3 with sufficient thrust or force represented by arrow 8 and maintain this force in order to rotate the prosthetic mitral valve 1. Since the prosthetic mitral valve 1 is located in the plane KLMN which is not directly accessible from the patient's open chest and, in fact, is disposed downwardly toward the operating table at an acute angle, rotation of the prosthetic mitral valve 1 is difficult. To clarify the limited space with which the surgeon must work with, for an average man, the opening 2 may be only five inches long (line segment AD) and one and one-half inches wide (line segment AP). Access to the atrium 3 in plane GHIJ is approximately two and one-half to three inches from the opening 2 and approximately one and one-half inches from the right lung (plane ADEF). The atrium 3 is approximately one and one-half inches long. Of course, each of the foregoing dimensions is less for a smaller patient such as a child.

U.S. Pat. No. 5,403,305 discloses a prosthetic heart valve rotating device. The device includes an eccentric socket attached to a bendable shaft. The eccentric socket receives a rotator head. A spring retains the rotator head in the socket. Since an axis of the socket and rotator head is offset from the bendable shaft, rotation of the prosthetic heart valve requires rotation of the shaft about the axis of the rotator head.

SUMMARY OF THE INVENTION

An aspect of the present invention is a prosthetic heart valve rotator tool that will operate in the small chest cavity available to the surgeon, having parts that can be easily assembled and disassembled, allowing it to be cleaned and sterilized for repeated use.

In an embodiment, the prosthetic heart valve rotator tool includes an elongated shaft and a first gear mounted on one end of the elongated shaft. A drive shaft has a first end that is positional proximate the prosthetic heart valve and a second gear mounted on a second end of the drive shaft. A support structure holds the first gear and the second gear in a mating position and is separable to allow removal of the first gear and the second gear for sterilization.

Another aspect of the present invention is a prosthetic heart valve rotator tool having an operator actuated member, a rotator engageable with a prosthetic heart valve for selectively rotating the prosthetic heart valve, and a coupler for coupling the rotator to the operator actuated member to selectively rotate the rotator about an axis of the rotator and selectively displace the axis and the rotator relative to the operator actuated member.

BRIEF DESCRIPTION OF THE DRAWINGS

FIG. 4 is a side elevational view of a second embodiment of a prosthetic heart valve rotator tool.

FIG. 5 is a perspective view of the prosthetic heart valve rotator tool of FIG. 4.

FIG. 7 is a perspective view of a third embodiment of a prosthetic heart valve rotator tool.

FIG. 7A is a perspective view of a locking mechanism and a portion of a shaft of the embodiment of FIG. 7.

FIG. 8 is a perspective view of a fourth embodiment of a prosthetic heart valve rotator tool.

FIG. 10 is a perspective view of a sixth embodiment of a prosthetic heart valve rotator tool.

FIG. 11 is a perspective view of a seventh embodiment of a prosthetic heart valve rotator tool.

FIG. 12 is a perspective view of an eighth embodiment of a prosthetic heart valve rotator tool.

DETAILED DESCRIPTION OF THE PREFERRED EMBODIMENTS

Figure 1:
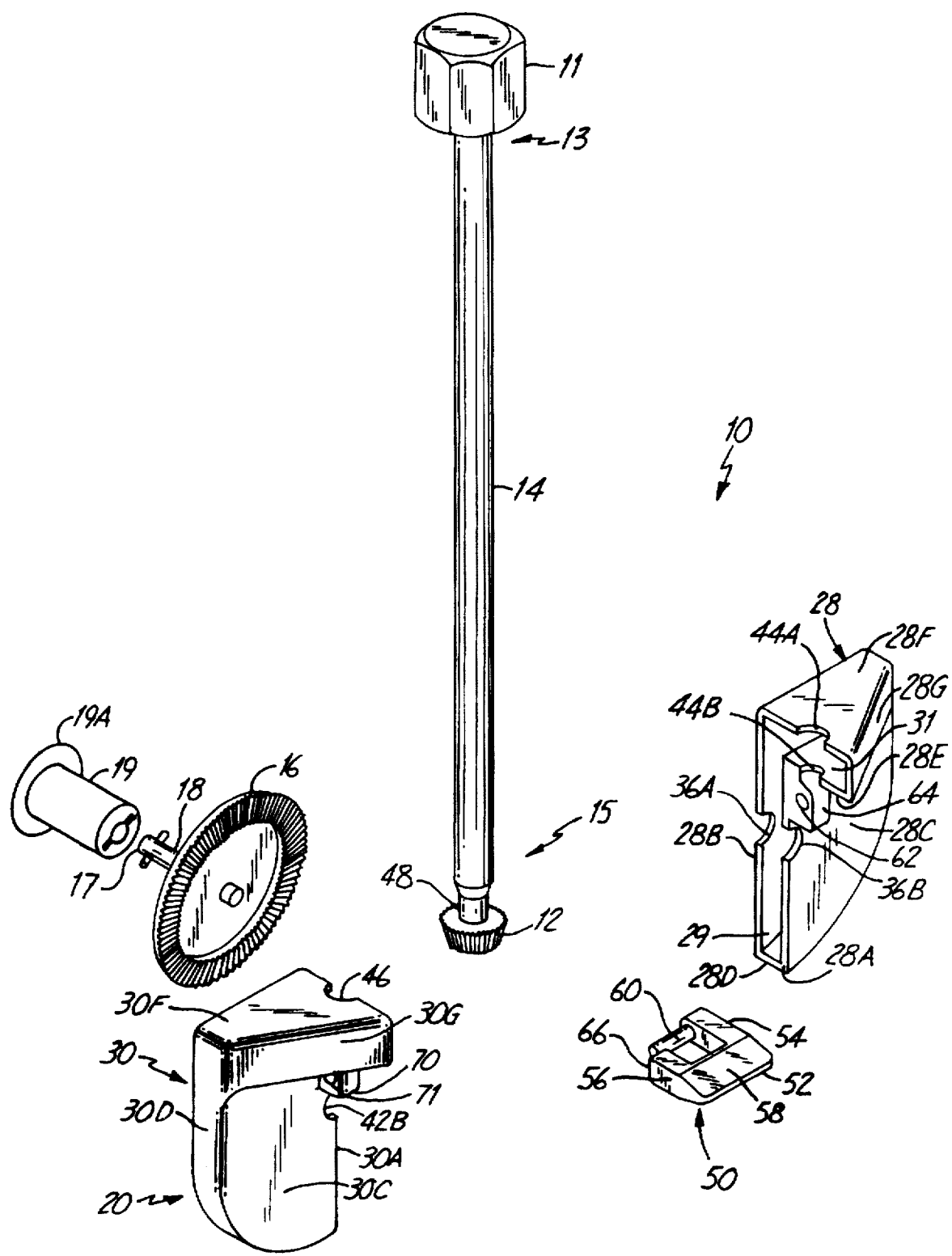
FIG. 1 is an exploded perspective view of a prosthetic heart valve rotator tool of the present invention.
Figure 2:
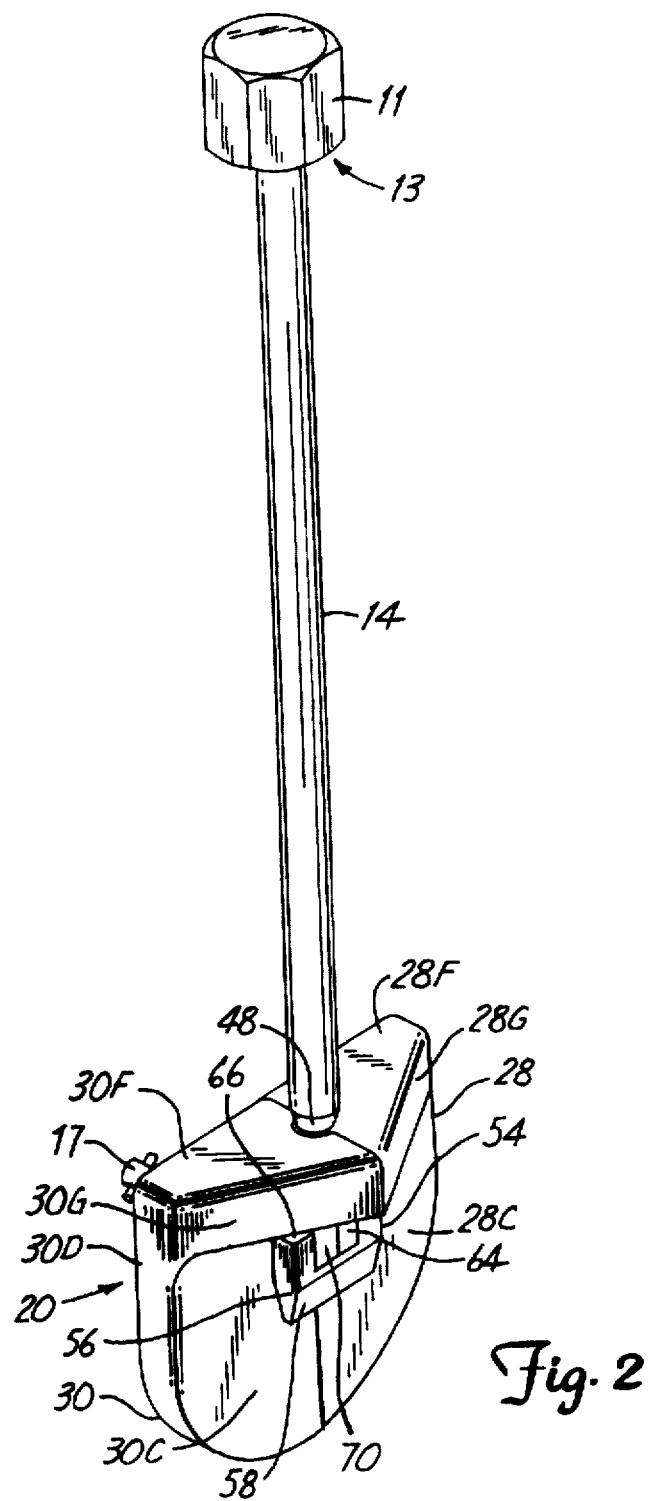
FIG. 2 is an assembled perspective view of the prosthetic heart valve rotator tool of FIG. 1.

FIGS. 1 and 2 illustrate a first embodiment of a prosthetic heart valve rotator tool 10 of the present invention suitable for rotating a prosthetic heart valve, not shown, after it has been implanted. The prosthetic heart valve rotator tool 10 includes a rigid elongated shaft 14 having a knob 11 mounted on a proximal end 13 and a first gear 12 mounted on a distal end 15. The first gear 12 mates with a second gear 16 mounted on a drive shaft 18. An end 17 of the drive shaft 18 is coupleable to a rotator 19 used to engage and rotate the prosthetic heart valve. By rotating the knob 11, a surgeon can easily rotate the rotator 19 through the mating gears 12 and 16. The prosthetic heart valve rotator tool 10 is compact and requires little space in order to operate and, therefore, will fit within the small chest cavity available to the surgeon. As will be described below, the prosthetic heart valve rotator tool 10 can be easily assembled and disassembled, allowing it to be cleaned and sterilized for repeated use.

Throughout the Figures and embodiments described below, the rotator 19 is generally depicted. Those skilled in the art will recognize that the rotator 19 includes a head 19A having a shape suitable for either prosthetic aortic valves or prosthetic mitral valves. Since prosthetic heart valves in general can be constructed with a single leaflet or with multiple leaflets, an outer surface of the rotator head 19A is shaped in a known manner to properly engage the specific prosthetic valve used during surgery. Since the rotator head 19A can be formed in any one of a number of shapes, throughout the Figures, the enlarged head 19A will generally represent these engaging surfaces.

Figure 3:
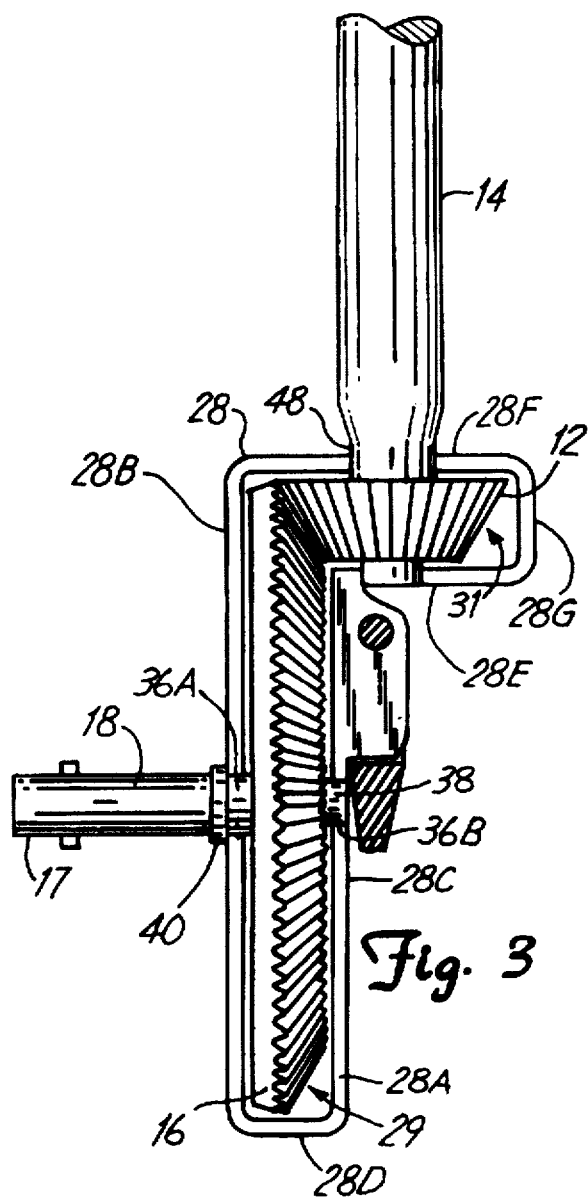
FIG. 3 is an enlarged sectional elevational view of a portion of the prosthetic heart valve rotator tool of FIG. 1 with parts removed.

Referring to FIGS. 1-3, the first gear 12 and the second gear 16 are held in mating relationship with each other by a support structure 20. The support structure 20 includes separable, preferably integral, portions 28 and 30. The portions 28 and 30 are selectively joined together and abut edge faces 28A and 30A, respectively, to form a housing that encloses the first gear 12 and the second gear 16. Referring first to portion 28, it is preferably an integral structure having a back surface 28B and a front surface 28C substantially parallel to the back surface 28B. The portion 28 also includes an interconnecting sidewall 28D that with the back surface 28B and the front surface 28C form a chamber 29, which receives half of the second gear 16. A wall portion 28E extends from the front surface 28C and with a wall portion 28F extending from back surface 28B and an inclined connecting wall portion 28G form a chamber 31 that receives half of the first gear 12.

The portion 30 is similar to the portion 28. A back surface 30B (the same surface of a second embodiment illustrated in FIG. 6), and a front surface 30C, substantially parallel to the back surface 30B, together with an interconnecting sidewall 30D form a chamber, not shown, but similar to chamber 29, that receives the remaining half of the second gear 16. A wall portion, not shown, but similar to the wall portion 28E, extends from the front surface 30C and with a wall portion 30F extending from the back surface 30B and an inclined connecting wall portion 30G form a chamber, not shown, but similar to chamber 31, that receives the remaining half of the first gear 12.

The support structure 20 holds the elongated shaft 14 and the drive shaft 18 in position to maintain mating contact between teeth of the first gear 12 and the teeth of the second gear 16. In the embodiment illustrated, the support structure 20 includes apertures formed when the portions 28 and 30 are joined together. In particular, semi-circular recesses 36A and 36B are provided in the front and back surfaces 28C and 28B, respectively. FIG. 3 illustrates the gears 12 and 16 in the portion 28. The recess 36B receives an end 38 of the drive shaft 18, while the recess 36A receives a portion of the drive shaft 18 proximate an annular flange 40. Corresponding semi-circular recesses 42A (same recess as the second embodiment illustrated in FIG. 6) and 42B (FIG. 1) are formed in the edge face 30A of the portion 30 to face the recesses 36A and 36B, respectively. Surfaces of the recesses 36A, 36B, 42A and 42B form bearing surfaces for the shaft 18.

Similarly, semi-circular recesses 44A and 44B in portion 28, and corresponding recesses formed in portion 30, one of which is illustrated at 46, form apertures and bearing surfaces for the elongated shaft 14 on opposite sides of the first gear 12. A reduced diameter portion 48 of the elongated shaft 14 helps maintain the axial position of the elongated shaft 14 in the support structure 20. The apertures supporting the shafts 14 and 18 and the chambers for the gears 12 and 16 formed by the portions 28 and 30 retain the gear train comprising gears 12 and 16 in only one orientation. This prevents improper assembly of the rotator tool 10.

A locking device 50, illustrated in FIG. 1, selectively holds the portion 28 and the portion 30 together. In the embodiment illustrated, the locking device 50 comprises a U-shaped clasp 52 that is removably secured to the portions 28 and 30. The U-shaped clasp 52 includes a first leg portion 54, a second leg portion 56, and an interconnecting center portion 58. A pin 60 is secured to the first leg portion 54 and extends toward the second leg portion 56. The second leg portion 56 is shorter than the first leg portion 54. The pin 60 is inserted through a bore 62 formed in a projection 64 extending from the front surface 28C. An end face 66 of the second leg portion 56 faces an upper surface of the projection 64 as the pin 60 is inserted through the bore 62. A projection 70 similar to the projection 64 extends from the front surface 30C and includes a bore 71 or at least a recess that receives the pin 60. The portions 28 and 30 are held together when the clasp 52 is rotated about an axis extending through the pin 60 toward the front surfaces 28C and 30C. As illustrated in FIG. 2, the first leg portion 54 and the second leg portion 56 hold the projections 64 and 70 together, which thus, holds the portions 28 and 30 together. Since the pin 60 extends through the projections 64 and 70, sliding movement of the portions 28 and 30 across the edge faces 28A and 30A, respectively, is also inhibited.

The prosthetic heart valve rotator tool 10 is preferably made from a suitable material such as stainless steel, or a polymer, such as polysulfone or polycarbonate, that allows each of the components to be cleaned, sterilized, including by steam sterilization, and easily assembled prior to use.

It should be understood that full enclosure of the first gear 12 and the second gear 16 within the portions 28 and 30 is not required. The first gear 12 and the second gear 16 can be mounted on a suitable support plate.

Figure 6:
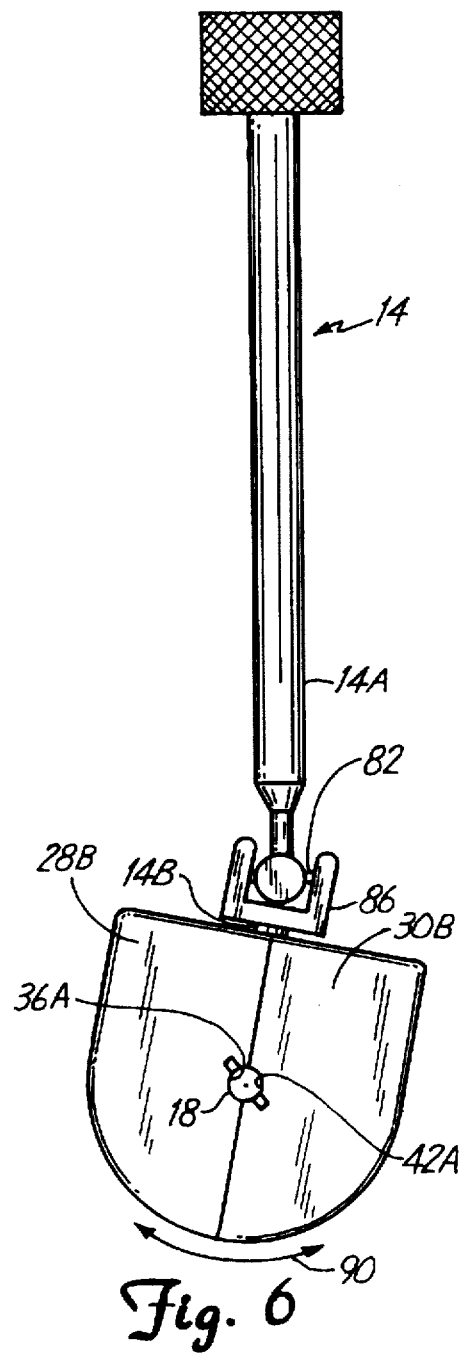
FIG. 6 is a rear elevational view of the prosthetic heart valve rotator tool of FIG. 4.

In a second embodiment illustrated in FIGS. 4-6, the elongated shaft 14 includes a pivotal coupling 80. The pivotal coupling 80 includes a pivot pin 82 formed on an end of a rod portion 14A. The pivot pin 82 extends between and into opposed slots 84A and 84B of a U-shaped member 86 formed on an end of a rod portion 14B. The first gear 12 is joined to the rod portion 14B on an end opposite the U-shaped member 86. As illustrated in FIGS. 4 and 6, the pivotal coupling 80 allows the drive shaft 18 to be rotated in two degrees of freedom through arcs indicated by double arrows 88 and 90 about the pin 82 and in a plane including an axis of the pin 82. A bracket 89 is attached to the portion 30 to allow the surgeon to grasp the prosthetic heart valve rotator tool 10 with a suitable surgical clamp proximate the drive shaft 18 to pivot the drive shaft 18 as desired and maintain a suitable force to rotate the prosthetic heart valve.

The embodiments illustrated in FIGS. 1-6 provide several advantages as a result of the features described above. The prosthetic heart valve rotator tool 10 can be disassembled, cleaned and sterilized repeatedly for use in multiple surgical procedures. Support structure 20 holds the shafts 14 and 18 in alignment so that the gears 12 and 16 mate together. However, the support structure is separable to allow removal of the gears 12 and 16 when the prosthetic heart valve rotator tool 10 is disassembled for sterilization. In addition, the support structure 20 conforms to the orientation of the gears 12 and 16 so that the support structure 20 is small in order that it can be easily inserted into and manipulated within the chest cavity.

FIG. 7 illustrates a third embodiment of a prosthetic heart valve rotator tool 100 of the present invention. The prosthetic heart valve rotator tool 100 includes an elongated shaft 102 rotatable at a proximal end 104 and a first gear 106 mounted on a distal end 108. The first gear 106 mates with a second gear 110 mounted on a drive shaft 112. The first gear 106 and the second gear 110 are selectively held in a mating relationship by a support structure 114. The support structure 114 includes a first gear housing 116 and a second gear housing 118. A hinge assembly 120 pivotally joins the first gear housing 116 with the second gear housing 118. The hinge assembly 120 includes a pivot pin 122. The teeth of the first gear 106 and the second gear 110 are of a suitable design to allow the gears 106 and 110 to mesh while the gear housings 116, 118 pivot on the pivot pin 122 through an arc indicated by double arrow 124. In this manner, the gears 106 and 110 remain in contact due to the shape of the teeth so that the surgeon can adjust the angle 124 to orient the shafts 102 and 112 to best accommodate the available space in the chest cavity.

Although each component of the prosthetic heart valve rotator tool 100 can be made of a suitable material such as plastic that allows the heart valve rotator tool 100 to be discarded after use, in an alternative embodiment, the prosthetic heart valve rotator tool 100 can be made of a suitable material such as a metal, for example, stainless steel, or a polymer and can be disassembled. In this manner, the components of the prosthetic heart valve rotator tool 100 can be repeatedly separated, cleaned, sterilized and reassembled for multiple surgical procedures.

In the embodiment illustrated, the first gear 106 is integrally joined to the shaft 102. The first gear 106 and shaft 102 can be removed from the first gear housing 116 by sliding the shaft 102 through a bore 125 and out through an aperture 126. Similarly, the second gear 110 and the shaft 112 are integrally formed together and can be removed from the second gear housing 118 by sliding the shaft 112 through a bore 128 and out an aperture 130. Preferably, the rotator 19 is removably secured to an end 134 of the shaft 112. The first gear housing 116 can be separated from the second gear housing 118 by removing the pin 122.

In a preferred embodiment, the first gear 106 and shaft 102 are removably secured in the first gear housing 116. In the embodiment illustrated, a locking mechanism 140 engages an outer surface of the shaft 102 after the shaft 102 has been inserted through the bore 125. The locking mechanism 140 retains the first gear 106 in the first gear housing 116, while allowing the first gear 106 and the shaft 102 to be rotated. Referring to FIG. 7A, in one embodiment, the locking mechanism 140 can include a suitable compliant inner ring member 142 that engages an annular groove 144 formed in the shaft 102. A second locking mechanism 148 engages the shaft 112 to retain the second gear 110 and the shaft 112 in position in the second gear housing 118. If desired, the locking mechanisms 140 and 148 can be integrally formed with the gear housings 116 and 118, respectively. Alternatively, the shafts 102 and 112 may not extend completely through each respective locking mechanism 140 and 148. In this manner, the locking mechanism 140 can be used as a knob. In addition, the rotator 19 can have an end that receives the shaft 112 wherein the rotator 19 forms a locking mechanism. It should also be understood that the gear housings 116 and 118 can be formed to completely enclose the gears 106 and 110, limiting the exposure to surrounding tissue.

The prosthetic heart valve rotator tool 100 provides a large range of motion between the shafts 102 and 112 in order to accommodate the small chest cavity. The prosthetic heart valve rotator tool 100 can be disassembled after each use and then cleaned, sterilized and reassembled again for another surgical procedure. Although illustrated wherein the gears 106 and 110 have a 1:1 ratio, other gear ratios can be used in order to easily rotate the rotator 19 or provide a mechanical advantage. The gear housings 116 and 118 retain the gears 106 and 110, and the shafts 102 and 112 in alignment from a straight position to a bent position. However, the gear housings 116 and 118 conform to the gears 106 and 110 to reduce the size of the prosthetic heart valve rotator tool 100 to operate without compromising the function of the prosthetic heart valve rotator tool 100.

FIG. 8 illustrates a fourth embodiment of a prosthetic heart valve rotator tool 160 of the present invention. The prosthetic heart valve rotator tool 160 includes a flexible elongated shaft 162 extending from a knob 164 to the rotator 19. The flexible shaft 162 extends through a flexible, stationary guide housing 168. The knob 164 is secured to or formed with the flexible shaft 162 on one end and secured to or formed with the rotator 19 at the other end. This prevents the housing 168 from sliding off either end. Removal of either the knob 164 or the rotator 19 allows removal of the flexible shaft 162 from the housing 168 to facilitate cleaning and sterilization. The shaft 162, the knob 164, the rotator 19 and the housing 168 can all be made from a suitable material such as plastic, metal or a combination thereof. In this manner, the prosthetic heart valve rotator tool 160 can be made to be reusable or disposable, as desired.

The flexible shaft 162 and the flexible housing 168 allow the prosthetic heart valve rotator tool 160 to be configured into an infinite array of odd positions. The rotator 19 rotates in the same direction as the knob 164, which makes it easy to use.

Figure 9:
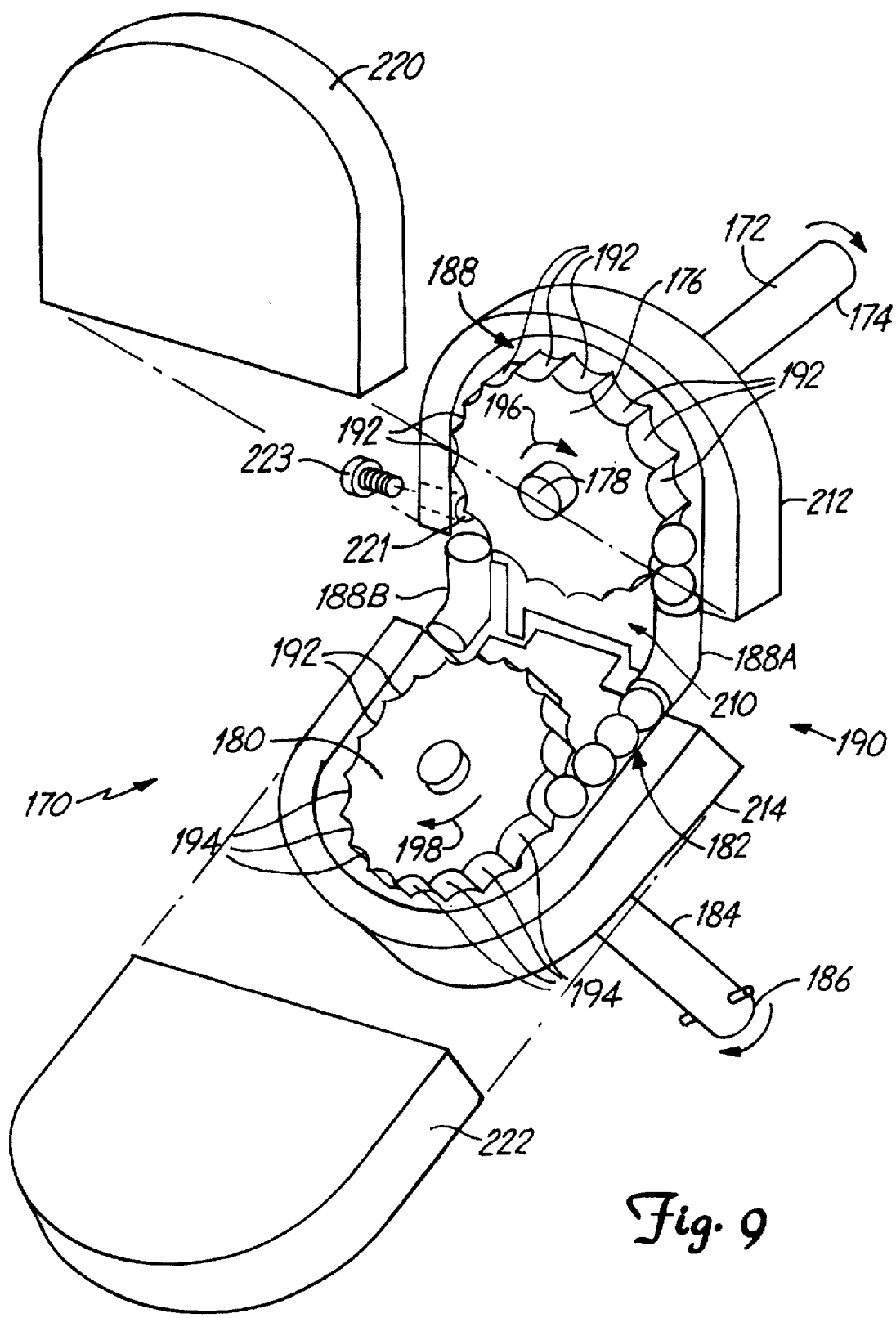
FIG. 9 is an exploded perspective view of a fifth embodiment of a prosthetic heart valve rotator tool.

FIG. 9 illustrates a fifth embodiment of a prosthetic heart valve rotator tool 170 of the present invention. The prosthetic heart valve rotator tool 170 includes an elongated shaft 172 rotatable at a proximal end 174 and a first gear 176 mounted on a distal end 178. The first gear 176 drives a second gear 180 through a plurality of individual drive elements, seven of which are indicated at 182. The second gear 180 is mounted on a drive shaft 184 having a remote end 186 that is coupleable to the rotator 19 (FIG. 1).

In the embodiment illustrated, the drive elements 182 are spherical balls that are guided in a channel 188 formed in a support structure 190. The channel 188 forms an endless loop between the first gear 176 and the second gear 180. It should be understood that a sufficient number of balls 182 are provided so that flexible conduits 188A and 188B of the channel 188 are filled with balls 182 and that sockets 192 of the first gear 176 and sockets 194 of the second gear 180 proximate the channel 188 also have balls 182. In this manner, as the first gear 176 is rotated, for example in a direction indicated by arrow 196, a driving force is exerted through the balls 182 which displaces the balls 182 in the channel 188 in order to rotate the second gear 180 in a direction indicated by arrow 198.

The portion 190 includes a suitable hinge assembly 210 which allows parts 212 and 214 to pivot relative to each other in order to translate a torque from the first gear 176 to the second gear 180. The flexible conduits 188A and 188B allow the drive balls 182 to pass between the parts 212 and 214. The flexible conduits 188A and 188B stretch and bend accordingly as the orientation of the parts 212 and 214 change. Plate members 220 and 222 enclose the channel 188. The plate member 220 attaches to the part 212 about the first gear 176, while the plate member 222, is attached to the part 214 about the second gear 180. With the plate members 220 and 222 secured, a threaded aperture 221 in the part 212 allows the plurality of balls 182 to loaded into the channel 188. After the plurality of balls 182 have been loaded, a threaded plug 223 closes the aperture 221.

FIG. 10 illustrates a sixth embodiment of a prosthetic heart valve rotator tool 230 of the present invention. The prosthetic heart valve rotator tool 230 includes an elongated handle 232 pivotally connected to a shaft 234 with a pivot pin 236. The rotator 19 for engaging a prosthetic heart valve, not shown, is coupleable to or integrally formed on an end 239 of the shaft 234. The pivot pin 236 allows the shaft 234 to pivot at a selected variable angle 240 with respect to the handle 232. Rotating the handle 232, for example, in the direction indicated by the arrow 250 results in rotational motion about the axis of shaft 234 in a direction indicated by arrow 252 thereby rotating rotator 19.

Preferably, the rotator 19 is coupled to the end 239 of the shaft 234 in any one of a plurality of selected angular positions about an axis of the rotator 19. In this manner, the rotator head 19A can be placed in the correct orientation so that it properly engages the prosthetic heart valve, while allowing the handle 232 to be placed in a position suitable for rotation by the surgeon. The shaft 234 can be of any desired length, but most importantly, it can be short so that the length of the shaft 234 and the rotator 19 can easily fit in the small chest cavity. The prosthetic heart valve rotator tool 230 can be made disposable or reusable. If necessary, the pivot pin 236 can be removed prior to cleaning and sterilization.

If desired, a bracket 231 is attached to the shaft 234 to allow the surgeon to grasp the prosthetic heart valve rotator tool 230 with a suitable surgical clamp to pivot the shaft 234 as desired and maintain a suitable force along the axis of the rotator 19.

FIG. 11 illustrates a seventh embodiment of a prosthetic heart valve rotator tool 260 of the present invention. The prosthetic heart valve rotator tool 260 includes an elongated handle 262 joined to a flexible shaft 264. The shaft 264 includes an end 266 that is coupleable to the rotator 19. Preferably, the flexible shaft 264 is made from a shape memory alloy such as nickel-titanium (NITINOL). This material is flexible and allows the shaft 264 to be bent at an angle suitable for insertion into the chest cavity and to engage the rotator 19 with the prosthetic heart valve. The shaft 264 can be bent as many times as desired during surgery. After surgery, the rotator 19 is removed and the handle 232 and flexible shaft 264 can be cleaned and sterilized. The shape memory alloy is particularly advantageous because it will return to its original shape once heated. Preferably, during sterilization, the flexible shaft 264 is heated to a temperature to cause the shaft 264 to return to its original state, for example, straight as indicated with dashed lines.

FIG. 12 illustrates an eighth embodiment of a prosthetic heart valve rotator tool 280 of the present invention. As illustrated, the prosthetic heart valve rotator tool 280 includes the elongated handle 232 pivotally connected to the shaft 234 with the pivot pin 236, as described above. However, in this embodiment, pivotally connected to the shaft 234 with the pivot pin 236, as described above. However, in this embodiment, a drive member 282 is selectively engageable with the shaft 234. The drive member 282 has an end 284 that is coupleable to the rotator 19. Alternatively, if desired, the drive member 282 and the rotator 19 can be integrally formed together to provide a single unitary piece. As described below, an end 286 of the shaft 234 includes a mating surface 288 that can be selectively coupled with a complimentary mating surface 290 formed on the drive member 282 so that rotation of the handle 232 and the shaft 234 causes rotation of the drive member 282.

Figure 13:
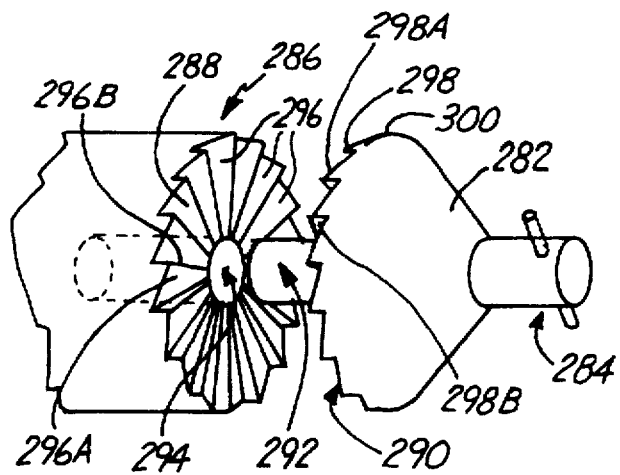
FIG. 13 is an enlarged perspective view of a portion of the embodiment of FIG. 12.

Referring also to FIG. 13, preferably, the drive member 282 includes a shaft portion 292 extending in a direction away from the end 284. An aperture 294 provided on the end 286 is of size and shape to receive the shaft portion 292. In the embodiment illustrated in FIGS. 12–13, the mating surface 288 comprises a plurality of wedge-shaped drive elements 296 disposed about the aperture 294 and the axis of the shaft 234. Each drive element 296 includes an inclined surface 296A and a suitable surface 296B that will couple with the mating surface 290 in order to rotate the drive member 282 when the shaft 234 is rotated about its axis. In the embodiment illustrated, the mating surface 290 also comprises a plurality of wedge-shaped drive elements 298 disposed on a surface 300 facing the mating surface 288. Each drive element 298 includes an inclined surface 298A and a surface 298B that couples with each of the surfaces 296B.

The mating surfaces 288 and 290 engage each other in order that torque is transmitted to the drive member 282 with rotation of the shaft 234. Specifically, rotation of the handle 232 in a direction indicated by arrow 306 causes the drive member 282 to rotate with the shaft 234 in a direction indicated by arrow 308, which in turn, allows the rotator 19 to rotate the prosthetic heart valve, not shown. If in the event the prosthetic heart valve needs to be further rotated in the direction indicated by the arrow 308, but the handle 232 cannot be further rotated in the direction 306 because of space limitations, the surgeon can rotate the handle 232 in a direction indicated by an arrow 310 without causing drive member 282 to rotate in a direction opposite the arrow 308. In particular, when the handle 232 is rotated in the direction 310, the mating surfaces 288 and 290 do not positively engage, but rather, slide relative to each other on the surfaces 296A and 298A. In this manner, the surgeon can reposition the handle 232 for subsequent rotation in the direction indicated by the arrow 306, while applying an axial force along the shaft 234 to maintain engagement between the rotator 19 and the prosthetic heart valve. It should be understood that the length of the shaft 234, the length of the drive member 282 and the length of the rotator 19 are together of suitable length to operate in the small chest cavity.

Figure 14:
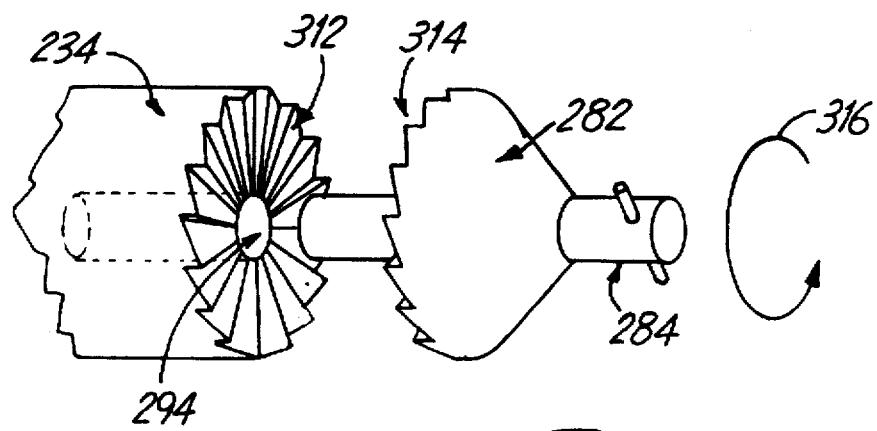
FIG. 14 is a perspective view of another embodiment of mating surfaces.

FIG. 14 illustrates mating surfaces 312 and 314 that engage each other similar to the mating surfaces 288 and 290, but allow rotation of the drive member 282 in a direction indicated by arrow 316.

Figure 15:
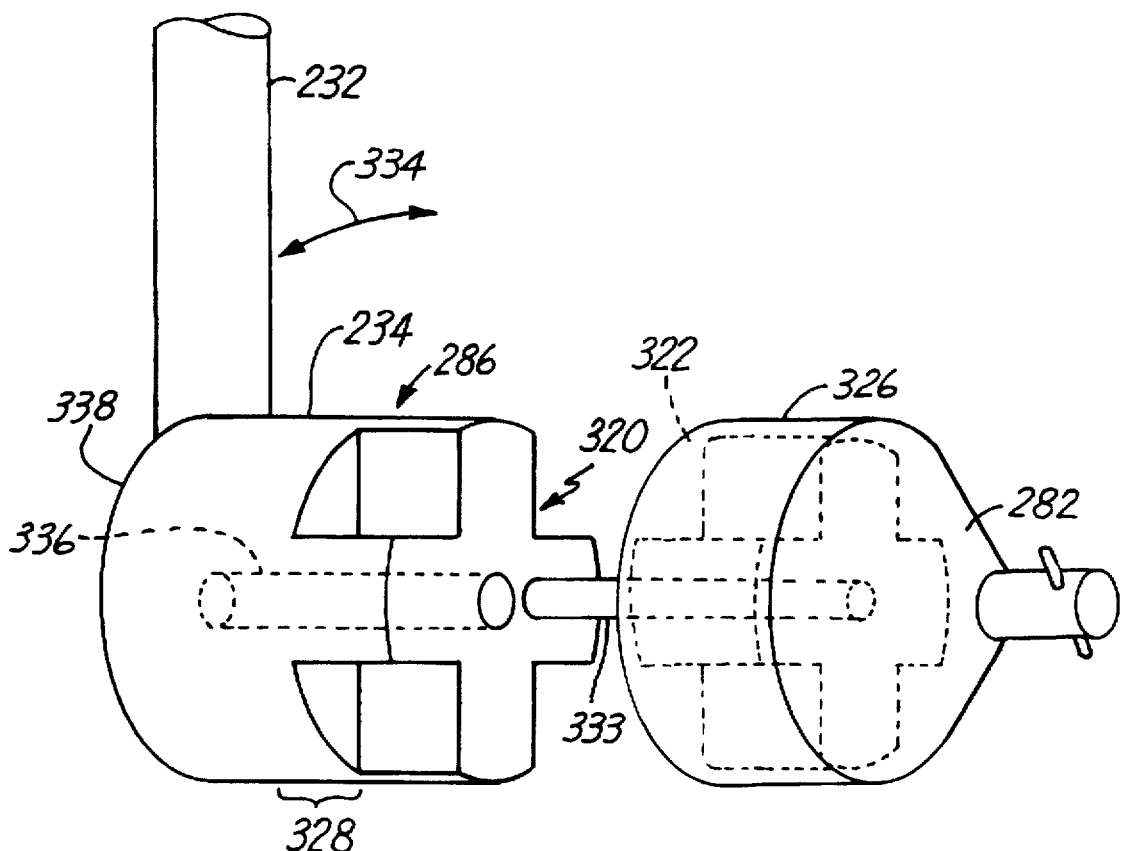
FIG. 15 is a perspective view of another embodiment of mating surfaces.
Figure 16:
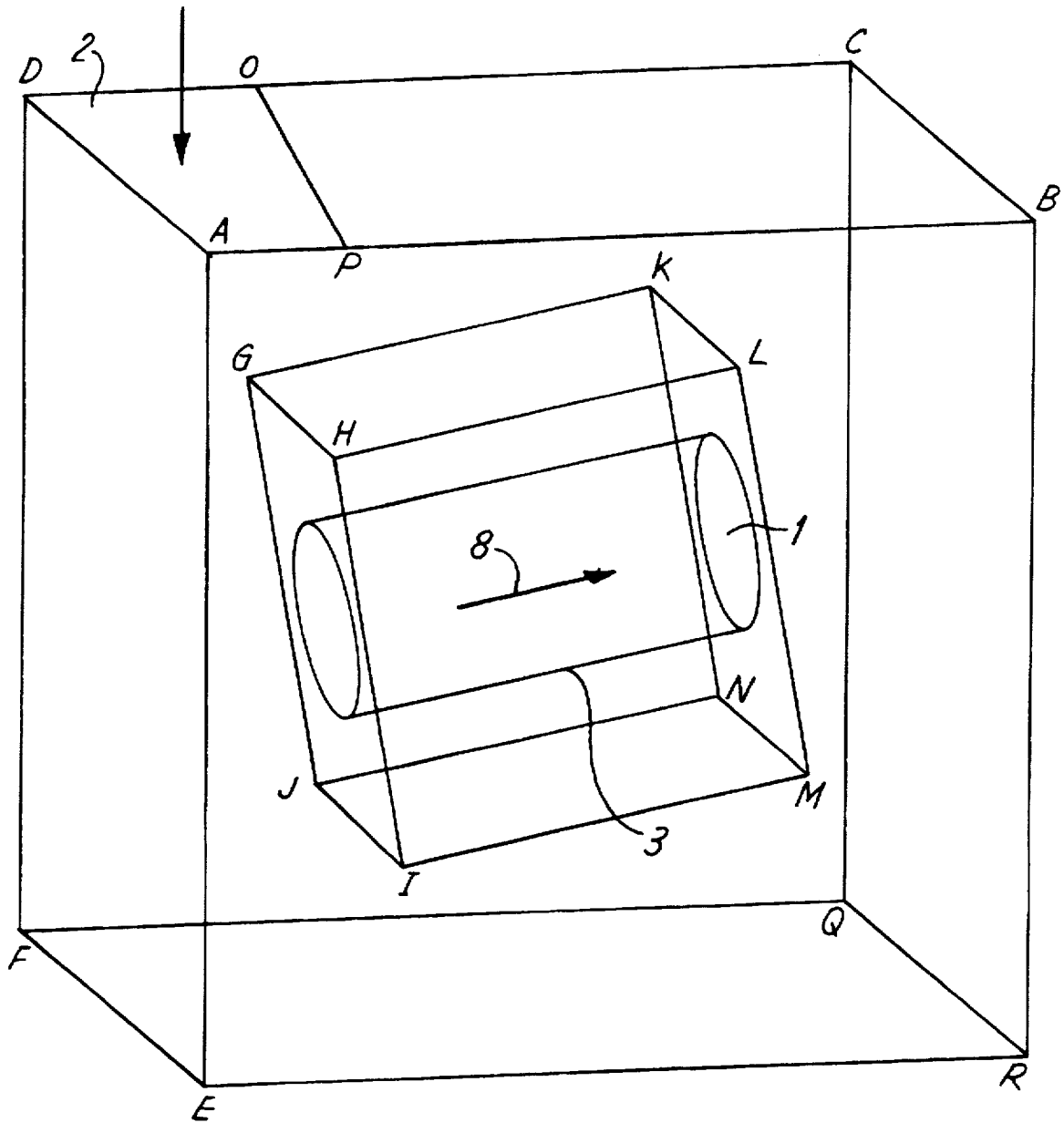
FIG. 16 is a schematic diagram representing a three dimensional view of a mitral valve in a patient's chest.

FIG. 15 illustrates another embodiment of coupleable mating surfaces 320 and 322. The mating surface 320 is provided on the end 286 of the shaft 234, while the mating surface 322 is formed on the drive member 282. In this embodiment, the mating surfaces 320 and 322 positively couple to each other so that with rotation of the shaft 234 in either direction as indicated by double arrow 334, the drive member 282 rotates along with the shaft 234.

The drive member 282 can include a sleeve portion 326 surrounding the mating surface 322. The sleeve portion 326 has an inside diameter that allows the sleeve portion 326 to slide over a portion 328 of the shaft 234 adjacent the mating surface 320. The sleeve portion 326 is of suitable length to allow the surgeon to decouple the mating surfaces 320 and 322 in order to reposition the handle 232, while maintaining alignment of the shaft 234 and the drive member 282, similar to the manner in which the shaft portion 292 interacts with aperture 294, of the previous embodiment. The sleeve portion 326 limits exposure of the mating surfaces 320 and 322 to the surrounding tissue.

It should be understood that the handle 232 and the shaft 234 can be integrally formed together without the pivot pin 236, as illustrated in this embodiment.

If desired, the drive member 282 can include a shaft portion 333, similar to the shaft portion 292, which extends through a bore 336 formed in the shaft 234 so that it extends beyond an end surface 338. In this manner, the surgeon can apply an axial force to the drive member 282 through the shaft portion 333, and thus, to the rotator 19 to maintain engagement of the rotator 19 with the prosthetic heart valve while the mating surfaces 320 and 322 are decoupled and the handle 232 is repositioned. It should be understood that if the shaft portion 333 is present, the sleeve portion 326 is also optional.

Although the present invention has been described with reference to preferred embodiments, workers skilled in the art will recognize that changes may be made in form and detail without departing from the spirit and scope of the invention.

What is claimed is:

1. A reusable prosthetic heart valve rotator tool for orienting a prosthetic heart valve in a patient, the rotator tool comprising:

an elongated shaft having a distal end;

a first gear mounted at the distal end of the elongated shaft;

a drive shaft having a first end positionable proximate the prosthetic heart valve;

a second gear mounted on a second end of the drive shaft; and a support structure having separable Portions for holding the first gear and the second gear in a mating position when joined together where the elongated shaft and the drive shaft are non-parallel and where separation of the separable portions causes disengagement of the first gear from the second gear and removal of the gears from the support structure for sterilization of the first gear, the second gear and the support structure.

2. The reusable prosthetic heart valve rotator tool of claim 1 and a rotator coupleable to the first end of the drive shaft.

3. The reusable prosthetic heart valve rotator tool of claim 1 and a clasp for selectively securing the separable portions.

4. The reusable prosthetic heart valve rotator tool of claim 3 wherein the clasp comprises a U-shaped locking element having a first leg longer than a second leg.

5. The reusable prosthetic heart valve rotator tool of claim 4 wherein the clasp includes a pin extending from the first leg toward the second leg.

6. The reusable prosthetic heart valve rotator tool of claim 1 wherein the separable portions form an aperture through which one of the shafts extends when the separable portions are joined together.

7. The reusable prosthetic heart valve rotator tool of claim 6 wherein the support structure comprises a housing, said separable portions comprising housing a first portion joinable to a second portion wherein the housing encloses at least a portion of the first gear and at least a portion of the second gear.

8. The reusable prosthetic heart valve rotator tool of claim 7 wherein the housing conforms to the first gear and the second gear in the mating position.

9. The reusable prosthetic heart valve rotator tool of claim 7 wherein facing surfaces of the first portion and the second portion include recesses forming a first aperture for the elongated shaft and a second aperture for the drive shaft.

10. The reusable prosthetic heart valve rotator tool of claim 4 wherein walls of the apertures form bearing surfaces.

11. The reusable prosthetic heart valve rotator tool of claim 7 wherein each separable portion forms a first chamber for receiving the first gear and a second chamber for receiving the second gear.

12. A prosthetic heart valve rotator tool comprising:

an operator actuated member;

a rotator engageable with a prosthetic heart valve for selectively rotating the prosthetic heart valve; and means for coupling the rotator to the operator actuated member to selectively rotate the rotator about an axis of the tool and selectively displace the axis and the rotator relative to the operator actuated member, wherein the means for coupling comprises a first gear secured to the operator actuated member; a second gear secured to the rotator; and a support structure having separable portions for forming an aperture through which at least one of the operator actuated member and the rotator extends and for retaining the first gear and the second gear in a mating position when the separable portions are joined together.

* * * * *

UNITED STATES PATENT AND TRADEMARK OFFICE
CERTIFICATE OF CORRECTION

PATENT NO.    :   5,788,689
DATED         :   August 4, 1998
INVENTOR(S)   :   Allan et al.

It is certified that error appears in the above-indentified patent and that said Letters Patent is hereby corrected as shown below:

ON THE TITLE PAGE:

Item [75] Inventors:

Delete "Kimberly A. Anderson, Eagan; William R. Holmberg, St. Paul; Kurt D. Krueger, Stacy; Michael J. Girard, Lino Lakes; Thomas G. Schoon, Cedar; Gary G. Rushmeyer, Marine of St. Croix, all of"

Column 10, line 31, delete "housing".

Column 10, lines 54-55, delete "of the tool".

Signed and Sealed this

Twenty-second Day of February, 2000

Attest:

Q. TODD DICKINSON

Attesting Officer           Commissioner of Patents and Trademarks